(12) United States Patent
Chianelli et al.

(10) Patent No.: US 8,956,854 B2
(45) Date of Patent: Feb. 17, 2015

(54) LANDFILL METHANE ENHANCEMENT PROCESS

(75) Inventors: Russell R. Chianelli, El Paso, TX (US); Xiomara Carolina Chianelli, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 891 days.

(21) Appl. No.: 13/039,853

(22) Filed: Mar. 3, 2011

(65) Prior Publication Data

US 2011/0217747 A1 Sep. 8, 2011

Related U.S. Application Data

(60) Provisional application No. 61/310,058, filed on Mar. 3, 2010.

(51) Int. Cl.

| | | |
|---|---|---|
| *A61L 9/01* | (2006.01) | |
| *B09B 3/00* | (2006.01) | |
| *B09C 1/10* | (2006.01) | |
| *C02F 3/34* | (2006.01) | |
| *C07C 9/04* | (2006.01) | |
| *C12M 1/00* | (2006.01) | |
| *C10L 1/00* | (2006.01) | |
| *C12P 5/02* | (2006.01) | |
| *H02K 7/18* | (2006.01) | |

(52) U.S. Cl.
CPC .. *C07C 9/04* (2013.01); *C12M 1/00* (2013.01); *C10L 1/00* (2013.01); *C12P 5/02* (2013.01); *H02K 7/18* (2013.01); *Y02E 50/343* (2013.01); *Y10S 435/822* (2013.01); *Y10S 435/946* (2013.01)
USPC ........ 435/262; 435/262.5; 435/266; 435/822; 435/946

(58) Field of Classification Search
None
See application file for complete search history.

(56) References Cited

U.S. PATENT DOCUMENTS

| | | |
|---|---|---|
| 5,288,170 A | 2/1994 | Cummings |
| 6,283,676 B1 | 9/2001 | Hater et al. |

*Primary Examiner* — Debbie K Ware
(74) *Attorney, Agent, or Firm* — Edwin S. Flores; Chalker Flores, LLP

(57) ABSTRACT

A zero-discharge landfill process is disclosed herein. The process described in the present invention recycles the exhaust gases from a combustion engine which reheats the landfill and provides moisture. Additionally, the $CO_2$ from the exhaust gases releases additional methane. Methane production in landfills can thus be enhanced by the method of the present invention. Furthermore, a portion of the exhaust gas can be used to cultivate algae in a cultivation tank. The cultivation of the algal species is enhanced in the presence of water, $CO_2$, CO, and the elevated temperatures. Optionally, a first portion of the cultivated algae can be passed through the landfill to increase methane production in the landfill and a second portion of the cultivated algae can be transferred to a biodiesel production tank, for the conversion of the one or more algal oils and lipids to a biodiesel or a biofuel by a transesterification reaction.

4 Claims, 2 Drawing Sheets

LANDFILL METHANE ENHANCEMENT PROCESS

CROSS-REFERENCE TO RELATED APPLICATIONS

This application claims priority to U.S. Provisional Application Ser. No. 61/310,058 filed Mar. 3, 2010, the entire contents of which are incorporated herein by reference.

TECHNICAL FIELD OF THE INVENTION

The present invention relates in general to the field of landfill methane generation, and more particularly to the development of a landfill methane enhancement process.

STATEMENT OF FEDERALLY FUNDED RESEARCH

None

REFERENCE TO A SEQUENCE LISTING

None.

BACKGROUND OF THE INVENTION

Without limiting the scope of the invention, its background is described in connection with landfill methane generation and enhancement.

U.S. Pat. No. 5,288,170 issued to Cummings (1994) describes a gas-to-energy system featuring beneficial use of sludge in a landfill. The system includes a device for disposing waste in the landfill and a device for disposing sludge in the landfill with the waste. The system also includes a device for collecting gas produced within the landfill from the sludge mixed with the waste and a device for generating electrical energy from the collected gas. The generating device is in fluidic communication with the collecting device. The present invention is also a system for a landfill having a device for disposing waste in a landfill, for disposing sludge in the landfill with the waste, for collecting gas produced within the landfill from the sludge mixed with the waste and a device for separating the gas into components having a common molecular structure. The '170 patent further describes a method of operating a landfill.

U.S. Pat. No. 6,283,676 issued to Hater et al. (2001) discloses landfills including multiple lifts having horizontal piping layers and methods for their use to accelerate anaerobic and/or aerobic degradation of municipal solid waste to increase landfill capacity. The '676 patent provides a method for degrading solid waste that increases landfill density and capacity, a method for degrading solid waste that accelerates landfill aerobic and/or anaerobic degradation, a method for degrading solid waste that improves degradation by-product quality, and a method for reducing noxious landfill gas emissions.

SUMMARY OF THE INVENTION

The present invention describes a zero-discharge landfill process. The process described in the present invention recycles the exhaust gases from a combustion engine which reheats the landfill and provides moisture. Additionally, the $CO_2$ from the exhaust gases releases additional methane.

A method of increasing methane production in a landfill is discloses in one embodiment of the instant invention. The method comprises the steps of: (i) passing one or more gases comprising methane produced in the landfill through a generator, wherein the generator is a methane powered generator, (ii) operating the generator to produce an electric current, wherein the operation of the generator produces an exhaust gas stream comprising water, $CO_2$, and CO at an elevated temperature, and (iii) recycling a first portion of the exhaust gas stream to the landfill, wherein the recycled gas stream increases a temperature and a moisture content of the landfill and thereby increases methane production. The method as disclosed herein further comprises: recycling a second portion of the exhaust gas stream by passing through a tank comprising one or more algal species and nutrients, wherein the water, $CO_2$, CO, and the elevated temperatures cultivate the algal species in the tank, passing a first portion of the cultivated algae through the landfill to increase methane production in the landfill; passing a second portion of the cultivated algae to a biodiesel production tank, wherein one or more algal oils and lipids from the cultivated algae are converted to biodiesels by a transesterification reaction, and collecting the biodiesel produced in the production tank in a collection vessel.

In one aspect of the method of the present invention the algal species are selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis* and *Pleurochysis*.

In another aspect the electric current produced by the generator is used to operate machinery, supply power to an electric grid, power electrical devices or for other suitable applications. Yet another aspect describes a methane gas produced by the method of the instant invention.

In another embodiment the present invention provides for a method for producing a biodiesel or a biofuel from one or more algal species. The method comprises providing one of more algal species, wherein the algae are selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis* and *Pleurochysis* along with one or more nutrients in a cultivation tank. The gas stream is then passed at an elevated temperature comprising one or more components selected from water, $CO_2$, CO through the cultivation tank to cultivate the algae. The cultivated algae are transferred to a biodiesel production tank, wherein the cultivated algae produce the algal oils or lipids in the presence of $CO_2$, nutrients and light under aerobic conditions. In the final step the algal oils and lipids are converted to the biodiesel or the biofuel by a transesterification reaction in the biodiesel production tank. The method as disclosed herein comprises the optional step of transferring a portion of the cultivated algae to a landfill to increase methane production in the landfill. In one aspect the gas stream comprises an exhaust gas stream from a methane powered generator, wherein the methane powered generator is operated by a methane gas generated in the landfill. Another aspect describes a biodiesel or a biofuel produced by the method of the present invention.

In yet another embodiment the present invention provides a system for producing a biodiesel or a biofuel from one or more algal species comprising: (i) a cultivation vessel or a tank for growing the one or more algal species in a growth medium and in presence of one or more nutrients, wherein the cultivation tank or vessel comprises one or more inlets or conduits to allow a passage of a gas stream at an elevated temperature comprising one or more components selected from water, $CO_2$, CO through the cultivation tank or vessel to cultivate the algae, (ii) transferring the cultivated algae to a biodiesel production tank for production of algal oils or lipids by the cultivated algae in the presence of $CO_2$, nutrients and light under aerobic conditions, (iii) a harvesting vessel for harvesting the cultivated algae from the biodiesel production tank, (iv) a concentration tank for concentrating the algae by removal of the growth medium, (v) a lysing tank for releasing the produced algal oils or lipids by a lysing the one or more algal species, (vi) a separation vessel for separating the released algal oils or lipids from the other released cellular components, and (vii) a reaction vessel for converting the separated algal oils or lipids to a biodiesel, a fatty acid methyl ester (FAME), a biofuel or combinations and modifications thereof by a transesterification reaction.

In one aspect the one or more algal species are selected from the group consisting of diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis*, and *Pleurochysis*. The system as described hereinabove further comprises the optional step of transferring a portion of the cultivated algae to a landfill to increase methane production in the landfill. In another aspect the gas stream comprises an exhaust gas stream from a methane powered generator. In yet another aspect the methane powered generator is operated by a methane gas generated in the landfill. In another aspect the other released cellular components comprise neutral lipids, proteins, triglycerides, sugars or combinations and modifications thereof. In a related aspect the system further comprises the optional step of processing an algal biomass comprising the lysed algal cells after separation of algal oils or lipids by drying to be used as animal feed or for energy generation.

The present invention also discloses a system for generating electric current comprising: one or more waste management units, wherein the waste management units produce one or more gases comprising methane and one or more gas flares or gas stacks placed in or attached to the wate management units, wherein the gas flares or gas stacks are in fluid communication with a methane powered generator, wherein the operation of the generator in the presence of methane in the one or more gases generates the electric current. In a specific aspect the waste management unit is a landfill. In one aspect the operation of the generator produces an exhaust gas stream comprising water, $CO_2$, and CO at an elevated temperature. In another aspect the system further comprises the steps of: recycling a first portion of the exhaust gas stream to the waste management unit, wherein the recycled gas stream increases a temperature and a moisture content of the waste management unit and thereby increases methane production and recycling a second portion of the exhaust gas stream to cultivate one or more biological species by passing through a tank comprising the one or more biological species and nutrients, wherein the water, $CO_2$, CO, and the elevated temperatures cultivate the biological species in the tank. In yet another aspect the biological species comprises bacterial cells, viral cells, fungal cells, algal cells, protozoal cells, mammalian cells or any combinations thereof. In a specific aspect the biological species comprises algal cells selected from the group consisting of diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis*, and *Pleurochysis*.

In a related aspect the system further comprises the steps of: (i) passing a first portion of the cultivated algae through the waste management unit to increase methane production in the waste management unit, (ii) passing a second portion of the cultivated algae to a biodiesel production tank, wherein one or more algal oils and lipids from the cultivated algae are converted to biodiesels by a transesterification reaction, and (iii) collecting the biodiesel produced in the production tank in a collection vessel. In another aspect the electric current produced by the generator is used to operate machinery, supply power to an electric grid, power electrical devices or for other suitable applications.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
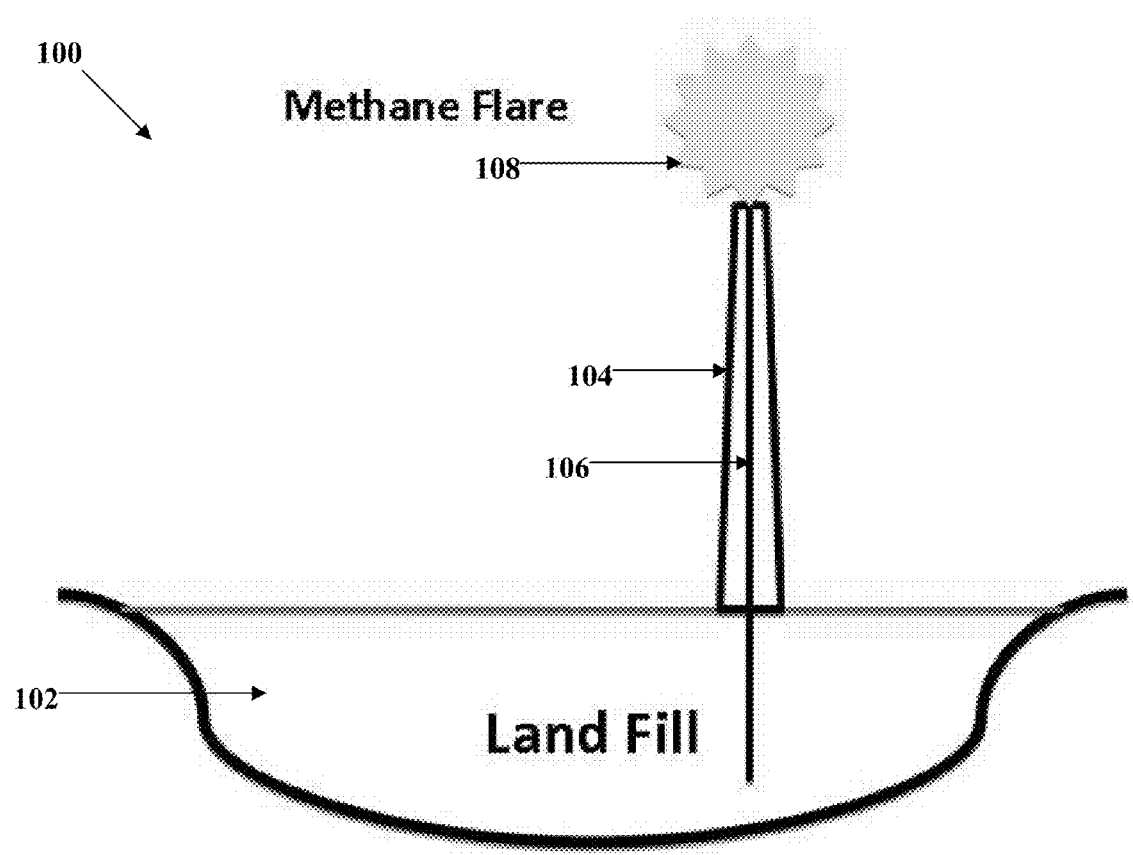
FIG. 1 shows a current (prior art) landfill process for generation of methane gas.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "landfill" as used herein refers to a site for the disposal of waste materials by burial. The term "landfills" may include internal waste disposal sites wherein a producer of waste carries out their own waste disposal at the place of production as well as sites used by many producers. Many landfills are also used for other waste management purposes, such as the temporary storage, consolidation and transfer or processing of waste material (sorting, treatment, or recycling). A "landfill" also may refer to ground that has been filled in with soil and rocks instead of waste materials, so that it can be used for a specific purpose, such as for building houses.

The term "methane" as used herein denotes not only pure methane, but also to natural gas compositions which are mainly methane but may contain minor proportions of other gases, for example helium, ethane and hydrogen sulfide. The term "methane" as used herein also extends to so-called synthetic natural gas i.e., methane produced by chemical synthesis and intended to be used as a replacement for natural gas. "Methane" may also refer to liquified natural gas (LNG) as it is produced either domestically or overseas. LNG is made by the pressurized and cooling liquifaction process as it is performed on natural gas coming out of the ground.

The term "exhaust gas" is used herein to denote a gaseous mixture, which results from combustion of a gaseous fuel with an oxidant. An oxidant may consist of air. An exhaust gas, resulting from combustion of a gaseous fuel with air, comprises nitrogen and carbon dioxide, if the gaseous fuel comprises at least one hydrocarbon. In addition to carbon dioxide and nitrogen, an exhaust gas may comprise oxygen, nitrogen oxides, water vapor, mechanical contaminants and other constituents.

As used herein the term "algae" represents a large, heterogeneous group of primitive photosynthetic organisms which occur throughout all types of aquatic habitats and moist terrestrial environments. Nadakavukaren et al., Botany. An Introduction to Plant Biology, 324-325, (1985). The term "algae" as described herein is intended to include the species selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira, Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis* and *Pleurochysis*.

As used herein the term "biodiesel and biofuel" oils encompass mixtures of petrochemical base diesel oils and renewable raw materials, although the ratio of petrochemical motor fuel to renewable raw materials in the mixture can vary and is not defined. The term "biodiesel" is also used for a variety of ester-based oxygenated fuels made from vegetable oils, fats, greases, or other sources of triglycerides. It is a nontoxic and biodegradable substitute and supplement for petroleum diesel.

The term "transesterification" as used herein refers to the reaction of exchanging an alkoxy group of an ester compound with another alcohol. The reaction may be acid or base catalyzed. In the present invention the transesterification process for preparation of a biodiesel involves an initial reaction of an oil, fat or grease with a solution of lithium base in a monohydric aliphatic alcohol to produce fatty alkyl esters and lithium alkaline glycerin. Optionally a co-solvent may be used during this transesterification reaction. The co-solvent is one in which all of the reactants are soluble so that the transesterification reaction occurs in one phase. The transesterification may be performed in a single reaction, or alternatively, the fatty ester portion may be reacted two or more times with the addition of further alcohol or further lithium base to ensure complete conversion. Following the transesterification reaction(s), the lithium alkaline glycerin, which is readily separated from the alkyl ester product, for example, by gravity separation in a reparatory funnel, is used to saponify fatty alkyl compounds to produce desalted glycerin and lithium soaps. The fatty alkyl esters, desalted glycerin and lithium soap may all be isolated and purified (if necessary) and used as, for example, commercial products.

The present invention teaches the recycle of the exhaust gases from the combustion engine. The exhaust gases are primarily water, $CO_2$ and CO at elevated temperatures. The recycle stream heats the landfill and provides moisture. Additionally, $CO_2$ will release additional methane as has been reported in coal mines. Nutrient gases may be added.

Waste methane is flared in most landfills. FIG. 1 shows a traditional landfill process 100 for generating methane gas. The landfill 102 comprises organic nutrients that produce methane that exits the landfill 102 through a gas flare or a vertical flare stack (pipe) 104. The methane gas 106 is flared (108) at the tip of the flare stack 104.

In some landfills methane is used to generate electricity via combustion engine coupled to generator. In this case the efficiency of the process depends on the amount of methane produced. The amount of methane can vary greatly. In a stable landfill the amount of methane produced depends on the temperature of the landfill, the moisture in the landfill and the amount of nutrients available. For example methane production can drop at night because of the drop in temperature in the landfill. This invention teaches the recycle of the exhaust gases from the combustion engine. The exhaust gases are primarily water, $CO_2$ and CO at elevated temperatures. The recycle stream heats the landfill and provides moisture. Additionally, $CO_2$ will release additional methane as has been reported in coal mines. Nutrient gases may be added.

Figure 2:
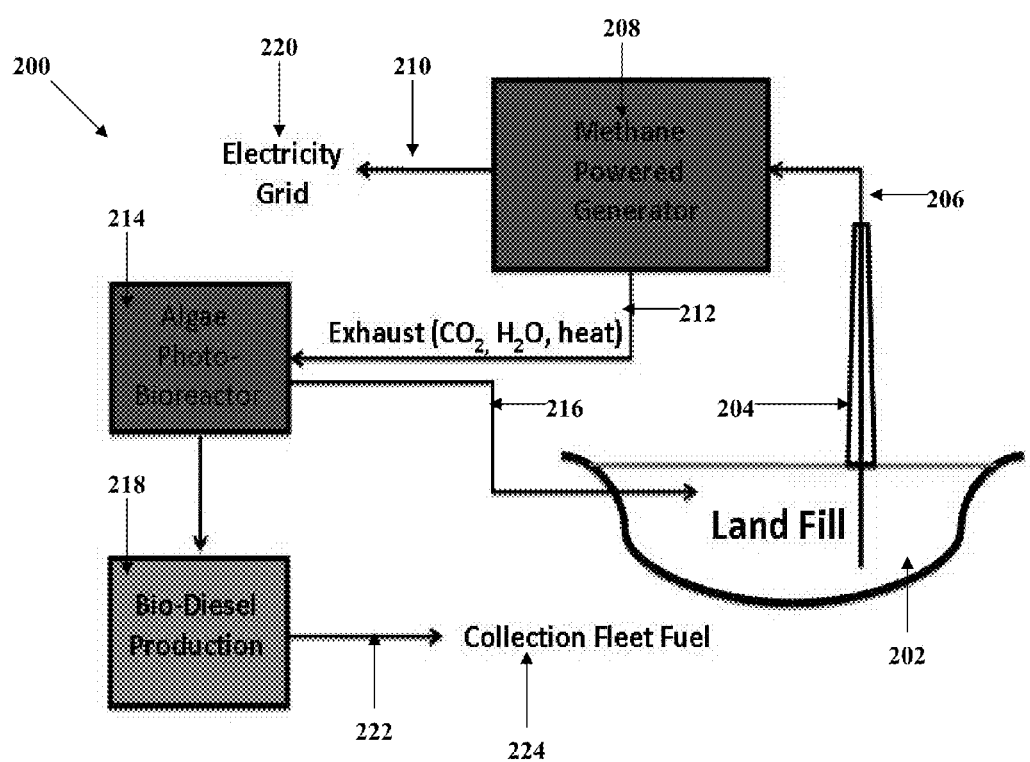
FIG. 2 shows a zero-discharge landfill according to certain embodiments of the present invention.

FIG. 2 shows a zero-discharge landfill 200 of the present invention. The landfill 202 generates methane gas 206 that passes through a gas flare or a vertical flare stack (pipe) 204 to run a methane powered generator 208. Electricity 210 generated by the operation of the generator 208 is used to run an electrical grid 220. The exhaust gas 212, generated from the operation of the generator 208 is fed to an algal photo-bioreactor 214 to grow and cultivate algae. The cultivated algae 216 are fed to the landfill 202 to produce methane 206. A fraction of the cultivated algae 216 is fed to a biodiesel production unit 218. The biodiesel 222 produced is collected in a collection vessel 224.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 5,288,170: Sludge/Waste Landfill Method and System.
U.S. Pat. No. 6,283,676: Sequential Aerobic/Anaerobic Solid Waste Landfill Operation.

What is claimed is:

1. A method of increasing methane production in a landfill comprising the steps of:
    passing one or more gases comprising methane produced in the landfill through a generator, wherein the generator is a methane powered generator;
    operating the generator to produce an electric current, wherein the operation of the generator produces an exhaust gas stream comprising water, $CO_2$, and CO at an elevated temperature; and
    recycling a first portion of the exhaust gas stream to the landfill, wherein the recycled gas stream increases a temperature and a moisture content of the landfill and thereby increases methane production.

2. The method of claim 1, further comprising the steps of:
    recycling a second portion of the exhaust gas stream by passing through a tank comprising one or more methanogenic algal species and nutrients, wherein the water, $CO_2$, CO, and the elevated temperature cultivate the algal species in the tank;
    passing a first portion of the cultivated algae through the landfill to increase methane production in the landfill;
    passing a second portion of the cultivated algae to a biodiesel production tank, wherein one or more algal oils and lipids from the cultivated algae are converted to biodiesels by a transesterification reaction; and
    collecting the biodiesel produced in the production tank in a collection vessel.

3. The method of claim 2, wherein the methanogenic algal species are selected from the group consisting of diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis*, and *Pleurochysis*.

4. The method of claim 1, wherein the electric current produced by the generator is used to operate machinery, supply power to an electric grid, power electrical devices or for other suitable applications.

* * * * *